US006532076B1

(12) United States Patent
Sidorowich

(10) Patent No.: US 6,532,076 B1
(45) Date of Patent: Mar. 11, 2003

(54) METHOD AND APPARATUS FOR MULTIDOMAIN DATA ANALYSIS

(75) Inventor: John J. Sidorowich, Santa Cruz, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 09/542,724

(22) Filed: Apr. 4, 2000

(51) Int. Cl.⁷ .............................. G01B 11/28; G06K 9/00
(52) U.S. Cl. ...................... 356/630; 382/141; 382/145
(58) Field of Search .................... 356/237.2–237.5, 356/630; 250/559.45; 382/141, 145, 147, 149

(56) References Cited

U.S. PATENT DOCUMENTS

| | | |
|---|---|---|
| 4,999,509 A | 3/1991 | Wada et al. |
| 5,148,513 A | 9/1992 | Koza et al. |
| 5,222,192 A | 6/1993 | Shaefer |
| 5,249,259 A | 9/1993 | Harvey |
| 5,255,345 A | 10/1993 | Shaefer |
| 5,343,554 A | 8/1994 | Koza et al. |
| 5,394,509 A | 2/1995 | Winston |
| 5,434,796 A | 7/1995 | Weininger |
| 5,493,401 A | 2/1996 | Horie et al. |
| 5,541,848 A | 7/1996 | McCormack et al. |
| 5,568,590 A | 10/1996 | Tolson |
| 5,581,657 A | 12/1996 | Lyon |
| 5,586,218 A | 12/1996 | Allen |
| 5,651,099 A | 7/1997 | Konsella |
| 5,694,474 A | 12/1997 | Ngo et al. |
| 5,864,633 A | 1/1999 | Opsal et al. |
| 5,896,294 A | 4/1999 | Chow et al. |
| 5,926,773 A | 7/1999 | Wagner |
| 5,953,446 A | 9/1999 | Opsal et al. ................. 382/141 |

OTHER PUBLICATIONS

R.A. Sequeira, R.L Olson, J.L. Willers & J.M. McKinion, "Automating the parameterization of mathematical models using genetic algorithms," *Computer and Electronics in Agriculture*, 1994, vol. 11, pp. 265–290.

E. Michielssen, S. Ranjithan R. Mittra, "Optimal multilayer filter design using real coded genetic algorithms," *IEE Proceedings–J*, Dec. 1992, vol. 139, No. 6, pp. 413–420.

(List continued on next page.)

*Primary Examiner*—Zandra Smith
(74) *Attorney, Agent, or Firm*—Stallman & Pollock LLP

(57) ABSTRACT

An optical measuring device generates a plurality of measured optical data from inspection of a thin film stack. The measured optical data group naturally into several domains. In turn the thin film parameters associated with the data fall into two categories: local and global. Local "genes" represent parameters that are associated with only one domain, while global genes represent parameters that are associated with multiple domains. A processor evolves models for the data associated with each domain, which models are compared to the measured data, and a "best fit" solution is provided as the result. Each model of theoretical data is represented by an underlying "genotype" which is an ordered set of the genes. For each domain a "population" of genotypes is evolved through the use of a genetic algorithm. The global genes are allowed to "migrate" among multiple domains during the evolution process. Each genotype has a fitness associated therewith based on how much the theoretical data predicted by the genotype differs from the measured data. During the evolution process, individual genotypes are selected based on fitness, then a genetic operation is performed on the selected genotypes to produce new genotypes. Multiple generations of genotypes are evolved until an acceptable solution is obtained or other termination criterion is satisfied.

37 Claims, 6 Drawing Sheets

OTHER PUBLICATIONS

T. Eisenhammer, M. Lazarov, M. Leutbecher, U. Schöffel & R. Sizmann, "Optimization of interference filters with genetic algorithms applied to silver–based heat mirrors," *Applied Optics*, Nov. 1, 1993, vol. 32, No. 31, pp. 6310–6315.

S. Martin, J. Rivory & M. Schoenauer, "Simulated Darwinian evolution of homogeneous multilayer systems: a new method for optical coatings design," *Optics Communications*, Sep. 1, 1994, vol. 110, No. 5/6, pp. 503–506.

K. Rabinovitch & G. Toker, "Genetic algorithm and thin–film design," *Proceedings SPIE*, Jul. 1994, vol. 2262, pp. 163–174.

S. Martin, J. Rivory & M. Schoenauer, "Synthesis of optical multilayer systems using genetic algorithms," *Applied Optics*, May 1, 1995, vol. 34, No. 13, pp. 2247–2254.

T. Bäck & Schütz, "Evolution Strategies for Mixed–Integer Optimization of Optical Multilayer Systems," *Proceedings Fourth Annual Conference on Evolutionary Programming*, 1995, pp. 33–51.

D.J. Mikulin, D.A. Coley & J.R. Sambles, "Fitting reflectivity data from liquid crystal cells using genetic algorithms," *Liquid Crystals*, 1997, vol. 22, No. 3, pp. 301–307.

M. Mitchell, "Genetic Algorithms: An Overview," *Complexity*, 1995, vol. 1, No. 1, pp. 31–39.

J.R. Koza, "Introduction to Genetic Algorithms," from *Genetic Programming*, Chapter 3, pp. 17–22 and 29.

J.H. Holland, "Genetic Algorithms," *Scientific American*, Jul. 1992, pp. 66–72.

R.L. Riolo, "Survival of the Fittest Bits," *Scientific American*, Jul. 1992, pp. 114–116.

J.T. Fanton, J. Opsal, D.L. Willenborg, S.M. Kelso & A. Rosencwaig, "Multiparameter measurements of thin films using beam–profile reflectometry," *J. Appl. Phys.*, Jun. 1, 1993, vol. 73, No. 11, pp. 7035–7040.

J. M. Leng, J.J. Sidorowich, .D. Yoon, J. Opsal, B.H. Lee, G. Cha, J. Moon & S.I. Lee, "Simultaneous measurement of six layers in a silicon on insulator film stack using spectrophotometry and beam profile reflectometry," *J. Appl. Phys.*, Apr. 15, 1997, vol. 81, No. 8, pp. 3570–3578.

E.A. Rietman & R.C. Frye, "A Genetic Algorithm for Low Variance Control in Semiconductor Device Manufacturing: Some Early Results," *IEEE Transactions on Semiconductor Manufacturing*, May 1996, vol. 9, No. 2, pp. 223–229.

J.F. Tang & Q. Zheng, "Automatic design of optical thin–film systems—merit function and numerical optimization method," *J. Opt. Soc. Am.*, Nov. 1982, vol. 72, No. 11, pp. 1522–1528.

Thomas Bäck et al., "Evolution Strategies for Mixed–Integer Optimization of Optical Multilayer Systems," *Proceedings of the Annual Conference on Evolutionary Programming*, 1995, pp. 33–51.

Ronaldo Antonio Sequeira et al., "Automating the parameterization of mathematical models using genetic algorithms," *Computers and Electronics in Agriculture*, vol. 11, 1994, pp. 265–290.

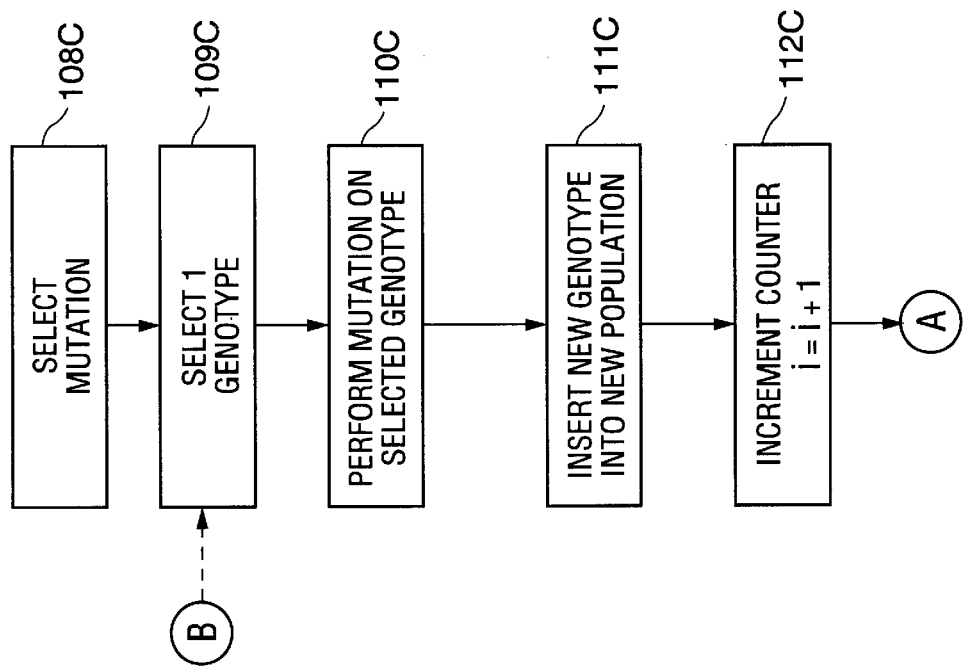
FIG. 5C
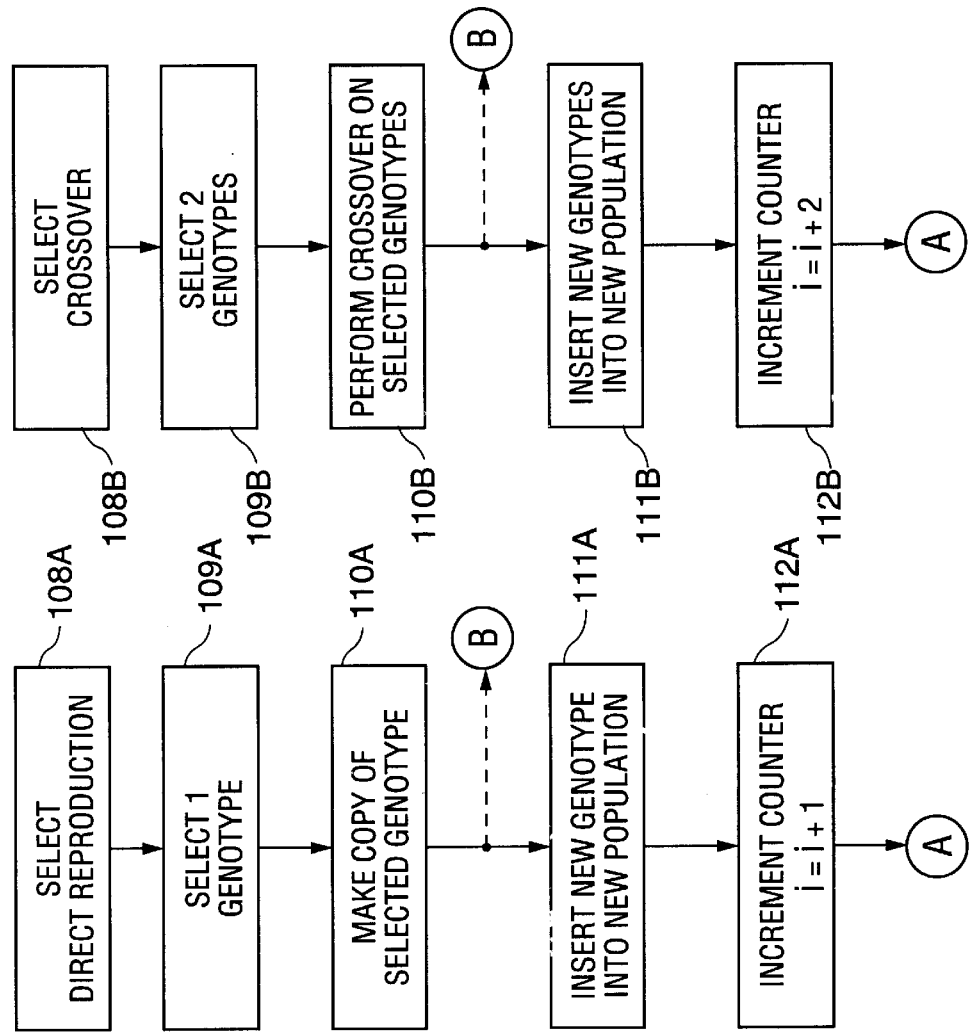
FIG. 5B
FIG. 5A

METHOD AND APPARATUS FOR MULTIDOMAIN DATA ANALYSIS

FIELD OF THE INVENTION

This invention relates to a multidomain method for evaluating the formation of thin films on semiconductor substrates using optical methods, and an apparatus embodying the method.

BACKGROUND OF THE INVENTION

Optical methods for measuring samples are generally known, in particular, for semiconductor fabrication involving the formation of a stack of thin film layers on a semiconductor substrate. Such methods are considered essential for the efficient operation of modern fabrication facilities. Optical methods are desirable because they are non-destructive and the resultant optical data can be used to derive information regarding layer parameters, such as thickness, refractive index, extinction coefficient, dispersion and scattering, for multiple layers of a thin film stack.

One preferred approach includes the use of the OPTIPROBE detector manufactured and sold by Therma-Wave, Inc. of Fremont, Calif., assignee herein, and described in part in one or more of the following U.S. Pat. Nos.: 4,999,014; 5,042,951; 5,181,080; 5,412,473; and PCT publication WO 99/02970, each of which is incorporated herein by reference in its entirety.

Conventional optical processing technology typically relies upon using a non-linear least squares algorithm to fit the measured data to a set of data points with a solution representing specific parameters of a thin film stack.

Improvements in optical technologies can provide an ever-increasing number of measured data points, which in turn provide the opportunity for deriving layer parameters on more complicated film stacks. However, this opportunity also presents a more complex optimization problem for developing solutions based on the observed data, and conventional processing techniques (such as least squares algorithms) are inadequate to handle the increased complexity.

Genetic Algorithms (GA's) have been applied to the problem of adaptive function optimization. A basic theoretical framework for GA's is described in Holland, *Adaptation in Natural and Artificial Systems* (1975). The terminology used by Holland is borrowed from genetics. Thus, in the computer analog, a GA is a method for defining a "population" of solutions to a selected problem, then evolving new populations by using probabilistic genetic operations to act on "individual" members of the population, i.e. individual solutions. Each individual in the population has a plurality of "genes," which are each representative of some real parameter of interest. For example, if there are x data parameters of interest, each individual would have x genes, and populations of individuals having x genes would be propagated by a GA.

The use of GA's for function optimization is generally described in U.S. Pat. Nos. 5,222,192 and 5,255,345, both to Schaefer. Further, U.S. Pat. No. 5,394,509 to Winston generally describes the application of GA's to search for improved results from a manufacturing process. Also, there has recently been much interest in the use of GA's in the design of various types of optical filters. See Eisenhammer, et al., *Optimization of Interference Filters with Genetic Algorithms Applied to Silver-Based Heat Mirrors, Applied Optics*, Vol. 32 at pp. 6310–15 (1993); and Back & Schütz, *Evolution Strategies for Mixed-Integer Optimization of Optical Multilayer Systems, Proceedings of the Fourth Annual Conference on Evolutionary Programming* at pp. 33–51 (1995).

More recently, GA's have been applied to the problem of evaluating thin films on semiconductor wafers. U.S. Pat. No. 5,864,633, hereby incorporated by reference in its entirety, describes the application of GA's to the problem of evaluating the characteristics of thin film layers with an optical inspection device. The present invention is directed to an improvement on the method disclosed in U.S. Pat. No. 5,864,633 involving a multidomain optimization technique.

SUMMARY OF THE INVENTION

The technique described in U.S. Pat. No. 5,864,633 relates to an invention useful for converting optical measurements at a point on a semiconductor wafer into a description of the thin films beneath that point on the wafer. This application describes a modification of the GA technique described in U.S. Pat. No. 5,864,633 in order to improve either the evaluation of wafer measurements at multiple points on a wafer or the evaluation of (possibly multiple) measurements of multiple wafers.

The present invention provides a suitable multidomain optimization technique for doing this wherein two or more populations of genotypes are used. In general one evolving genotype population is employed for each of the individual measurement points on the wafer. Flags are used to divide the genes of the genotypes into two categories or classes: local and global. Local genes represent parameters that are only associated with one domain whereas global genes represent parameters associated with more than one domain. More than one category of global gene may be employed.

By subdividing the genes into global and local categories and employing a migration step that allows genotypes to move among two or more domains, the present invention improves the evaluation of the sample compared with the method taught in U.S. Pat. No. 5,864,633. This is so because the present invention allows the optimization process to reflect the possibility that some parameters may be constant or nearly constant across multiple domains whereas others may not be.

Multiple generations of the genotypes in each domain are evolved until an acceptable solution is obtained. Using conventional Fresnel equations, a processor derives theoretical data from the theoretical parameters defining each of the genotypes. The derived theoretical data for a given genotype are compared with the actual measured data in accordance with a fitness function. The fitness function provides a measure of how close the derived theoretical data are to the measured data. Individual genotypes are then selected based on this fitness comparison. Genetic operations are performed on the selected genotypes to produce new genotypes. In addition to crossover, direct reproduction, and mutation operations, a migration step is performed that allows genotypes to migrate among two or more domains.

BRIEF DESCRIPTION OF THE DRAWINGS

FIGS. 5A through 5C are flow chart portions illustrating the use of different genetic operations.

DETAILED DESCRIPTION OF THE INVENTION

Figure 1:
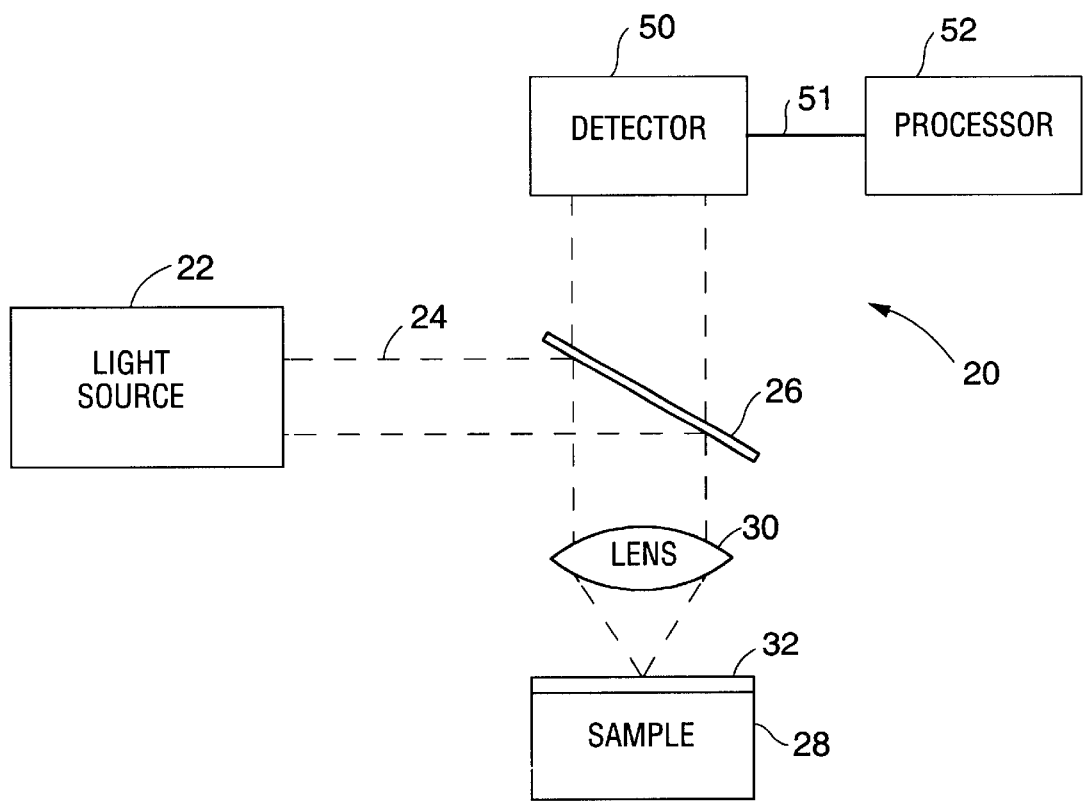
FIG. 1 is a block diagram illustrating a simplified optical inspection system.

FIG. 1 illustrates a block diagram for a basic optical inspection system 20 for measuring optical characteristics of a sample 28, such as a semiconductor wafer having one or more thin film layers 32 formed thereon. A light source 22 generates a probe beam of light 24 which is reflected by a beam splitter 26 through lens 30 onto the sample 28. The probe beam of light 24 is reflected off the sample 28 back through lens 30 and beam splitter 26 onto a photodetector 50. Photodetector 50 generates a plurality of outputs 51 which are supplied to a processor 52. The outputs are used to evaluate physical characteristics of the sample, and more particularly, of the thin film layer(s) 32 of the sample.

It will be appreciated by those skilled in the art that many configurations for an optical inspection system are possible, such as those described in U.S. Pat. Nos. 4,999,014; 5,042,951; 5,181,080; 5,412,473; and PCT publication WO 99/02970, each of which is incorporated herein by reference in its entirety. The preferred optical inspection system employs the OPTIPROBE detector manufactured and sold by Therma-Wave, Inc. of Fremont, Calif. These patents describe how measurements may be taken at multiple wavelengths and at multiple angles of incidence either simultaneously or serially. However, for the purpose of the present invention, it is sufficient to have an optical inspection system which generates multiple optical data measurements from the inspection of the semiconductor wafer.

An inspection system based on X-rays could also be used to generate the data measurements. A preferred X-ray inspection system is described in U.S. Pat. No. 5,619,548, issued Apr. 8, 1997, which is hereby incorporated by reference in its entirety.

The optical data measurements will typically take the form of amplitude information, such as reflectance versus angle of incidence, or reflectance versus wavelength, or polarization phase information, such as provided by ellipsometry. For example, the OPTIPROBE detector uses each of these techniques to take a large number of measurements in a single scan, then it filters the measured data resulting in from tens to hundreds of data points for each set of measurements.

Well known Fresnel equations can be used to predict or model the optical measurements expected from a known stack of layers with specified thicknesses, reflection indices and extinction coefficients. See Born & Wolf, *Principles of Optics*. However, the nature of the Fresnel equations is such that they cannot be easily inverted in order to unambiguously determine the various parameters of a thin film stack from a large number of multiple measured data points.

For this reason it is not easy to associate a correct set of theoretical parameters with measured data. Given a set of "theoretical" parameters which might correspond to the actual parameters of the stack to be evaluated, one can program a processor, using the Fresnel equations, to derive a set of theoretical data based on these theoretical parameters. The derived theoretical data may then be compared to the measured data and if there is a reasonable level of correspondence, one can assume that the generated theoretical parameters fairly describe the parameters of the thin film stack under investigation.

Of course, it would be highly unlikely that the first set of generated theoretical parameters, and the associated derived theoretical data, would provide a good match to the actual measured data. In the practice of the invention, the processor will generate thousands of sets of theoretical parameters. In accordance with the subject invention, the steps of generating the multiple sets of theoretical parameters are performed using a genetic algorithm.

Figure 2:
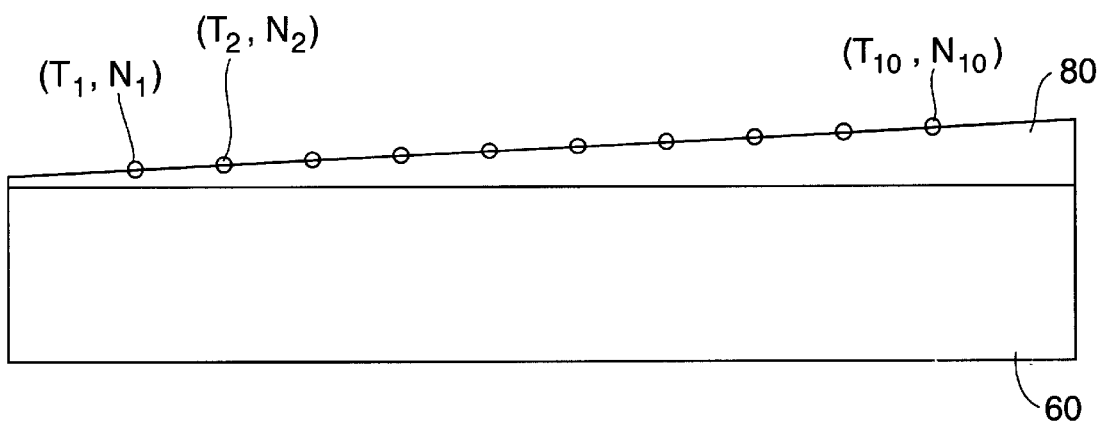
FIG. 2 shows a thin film sample on which a linescan of measurements has been made at 10 different points.

FIG. 2 illustrates an example of the type of problem that might be addressed by the present invention. FIG. 2 shows a sample with a dielectric thin film layer 80 on a substrate 60. The thickness of the thin film layer 80 increases in a continuous but unknown manner along the length of the sample. By way of example, one may wish to determine the thicknesses $T_i$ and indices of refraction $N_i$ of the thin film layer at multiple points on the sample rather than a single point. Given a linescan measurement that provides data at ten different points on the wafer, as shown in FIG. 2, it is desirable to ultimately parameterize the thin film thickness estimates on a point by point basis (10 parameters), but yet to ultimately parameterize a single value for the thin film index of refraction over all ten points (1 parameter).

According to the present invention, one optimizes the design of the genotypes to reflect the multidomain nature of the problem that one is addressing.

In the case of the FIG. 2 example, one would employ 10 domains or genotype populations, one corresponding to each point for which data was collected during the linescan. A genotype may be defined as an ordered set of genes, each gene representing a different thin film parameter of interest. In this example, each genotype would consist of an ordered pair of values $T_i$ and $N_i$, representing the thickness and index of refraction of the thin film layer at a given point, respectively. The initial population of genotypes for each domain can be varied based on the complexity of the problem and the amount of computation time and power available. By way of illustration, an initial population of 100 genotypes might be chosen for each of the 10 domains in the FIG. 2 example.

In accordance with the present invention, one classifies the individual genes as local or global. More than two categories of genes could also be employed. During the evolutionary GA process the global genes will be allowed to migrate among two or more domains. In the FIG. 2 problem, for example, one would classify the genes representing thickness as local and the genes representing index of refraction as global, since it may be assumed that the index is relatively constant. Typically the selection of genotypes for migration would be based partly on the fitness of the genotypes in which they occur and partly on chance. In other words, while random, the selection process would typically be weighted according to gentotype fitness. Migration of genotypes from a given domain associated with a given measurement point on the sample could be allowed to all other 9 domains or could be limited to domains associated with "neighboring" measurement points. Typically migrant genotypes received in a new domain would replace the least fit genotypes in the new domain. Alternatively, rather than migrating entire selected genotypes, the global genes from selected genotypes in a given domain could be used to replace corresponding global genes in selected genotypes in a new domain. In this alternative, then, global genes themselves, rather than entire genotypes, would in effect "migrate" by replacing the corresponding genes in selected genotypes in a new domain.

The GA process may be allowed to evolve until some termination criterion is satisfied. Such a termination criterion could involve the setting of a maximum number of generations, or a test for relative stability among the most fit, "elite" genotypes, or both. One expects that, as the domains evolve under the GA, the global genes of the elite genotypes in the different domains will tend to converge in value. In the case of the FIG. 2 problem, one would expect that at the end of the GA process the range of values for the global genes of the elite genotypes of the 10 domains would be much narrower than the range of values for the local genes of the elite genotypes. This reflects the physical fact that along the sample there is less variance in the index of refraction in the FIG. 2 thin film layer 80 than in its thickness.

Although the present invention is described in the context of genetic search algorithms, it could just also be applied to other kinds of iterative search algorithms (e.g., a neural network) that might be used to solve the multidomain problem of finding optimal parameter values for a semiconductor wafer sample. Given optical measurements made at different data points on a semiconductor wafer or wafer set, as long as some of the parameters are local in nature so that they should vary significantly between the data points, one would want to improve the search process by defining multiple search domains corresponding to the different measurement data points. And as long as some of the parameters are global in nature so that they should vary little between the data points, one would want to apply some type of cross-talk operation to improve the search process by communicating information about the global parameters among the different search domains as the search process proceeds.

Figure 3:
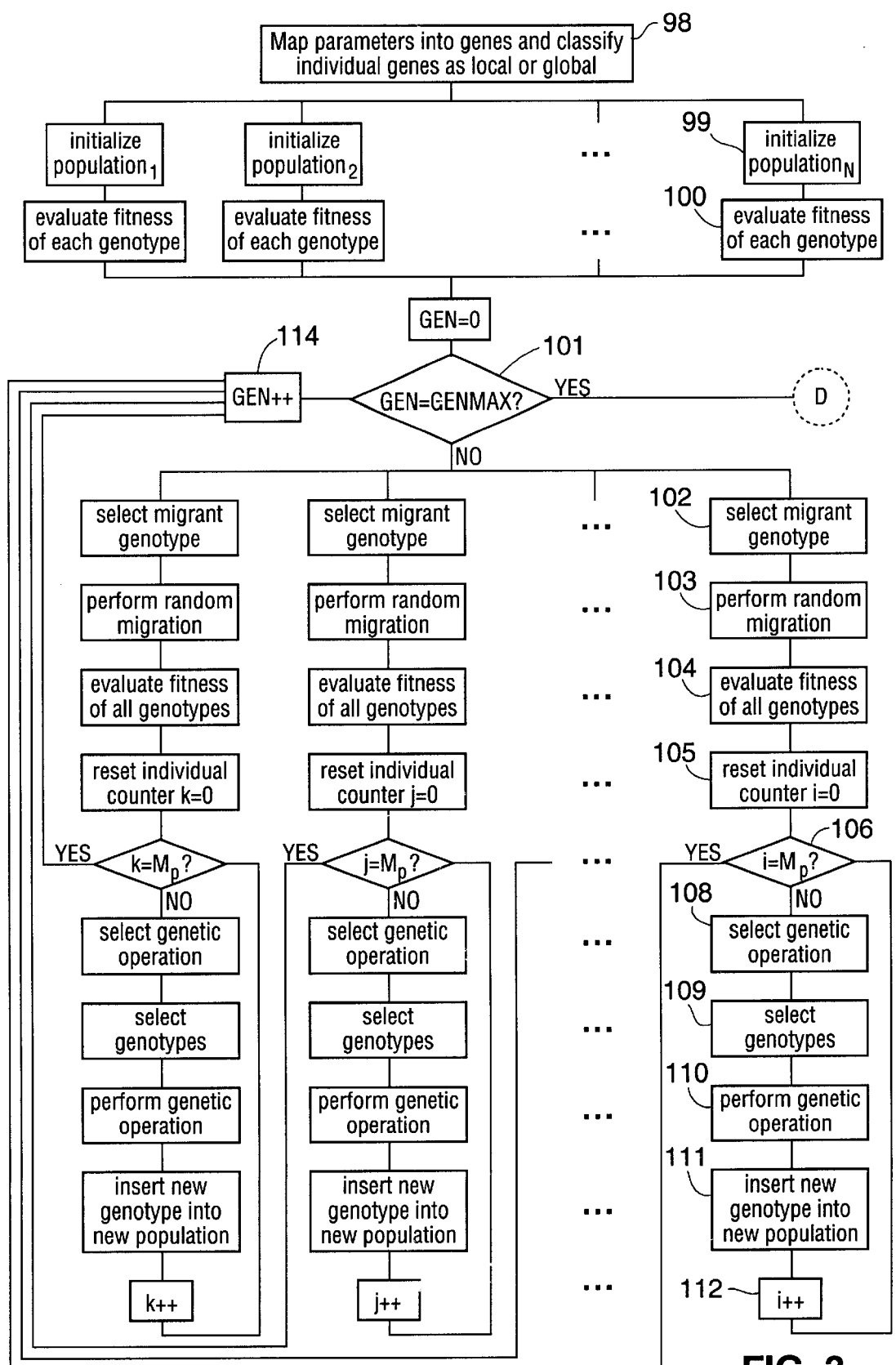
FIG. 3 shows a flow chart illustrating a portion of a method according to present invention.

Referring now to FIG. 3, a flow chart illustrates one method, which may be implemented in processor 52 with suitable programming, to carry out the present invention. It should be recognized that many variations in methodology could be used without affecting the scope of this invention. Processor 52 can be any general purpose computer having adequate computing resources for performing iterative processing. For example, a PENTIUM III processor running the LINUX operating system could be used.

In step 98, the set of thin film parameters to be optimized are chosen and mapped into a genotype. In practical terms, each parameter of interest or gene can be mapped into an individual data store, its range specified, and its contents supplied, altered, or otherwise operated on in accordance with suitable programming. The collection of individual data stores which store all the parameters of interest for a given measurement constitutes an individual genotype. It can be appreciated that the genotypes may be handled with common data processing commands to operate on the information stored therein for any suitable purpose. The present invention employs a GA to operate on selected genes to propagate additional genotypes having generally increasing fitness.

In addition in step 98 the genes are classified into local and global categories. As described above, global genes will be allowed to migrate among two or more domains. More than two categories of genes may be employed with the different categories of genes having different levels of migration privileges.

In step 99, a group of more than one initial populations, each comprising $M_p$ individual genotypes is created either at random or by arbitrary means. For example, the initial p populations may be initialized with preexisting data from prior measurements. The number of initial genotypes $M_p$ "seeded" into each of the p genotype populations is also arbitrary and may be chosen in light of the computer power available and the complexity of the problem.

The fitness of each genotype in the current populations is evaluated and stored for reference in step 100. The fitness is determined by a fitness function F, which is based on the parameters of interest. The fitness F may be defined as a function of the residual value between a measured data point $x_i$ and a theoretical data point $y_i$, for N measurements, for example:

F=(RES), e.g.
2-√RES
where $$RES = \sqrt{(1/N)\sum_{i=1}^{N}(x_i - y_i)^2}$$

One way in which the fitness F may be measured is to apply the Fresnel equations to the parameters of a genotype to get predicted values that can then be compared with the measurement values. Another way to measure fitness is to take the parameters of the genotypes as the starting point for performing an iterative nonlinear least squares optimization technique such as the well-known Marquardt-Levenberg algorithm. Fitness is then measured by comparing the values predicted by the results of the nonlinear least squares optimization technique to the measurement values. A suitable iterative optimization technique for this purpose is described in "Multiparameter Measurements of Thin Films Using Beam-Profile Reflectivity," Fanton et al., Journal of Applied Physics, Vol. 73, No. 11. p.7035 (1993) and "Simultaneous Measurement of Six Layers in a Silicon on Insulator Film Stack Using Spectrophotometry and Beam Profile Reflectometry," Leng et al., Journal of Applied Physics, Vol. 81, No. 8, p.3570 (1997). These two articles are hereby incorporated by reference in their entireties. Fitness could also be measured using the Fresnel equations directly sometimes and using a nonlinear optimization technique at other times.

The variable GEN is used to identify the generation number and is then initialized to zero.

Figure 4:
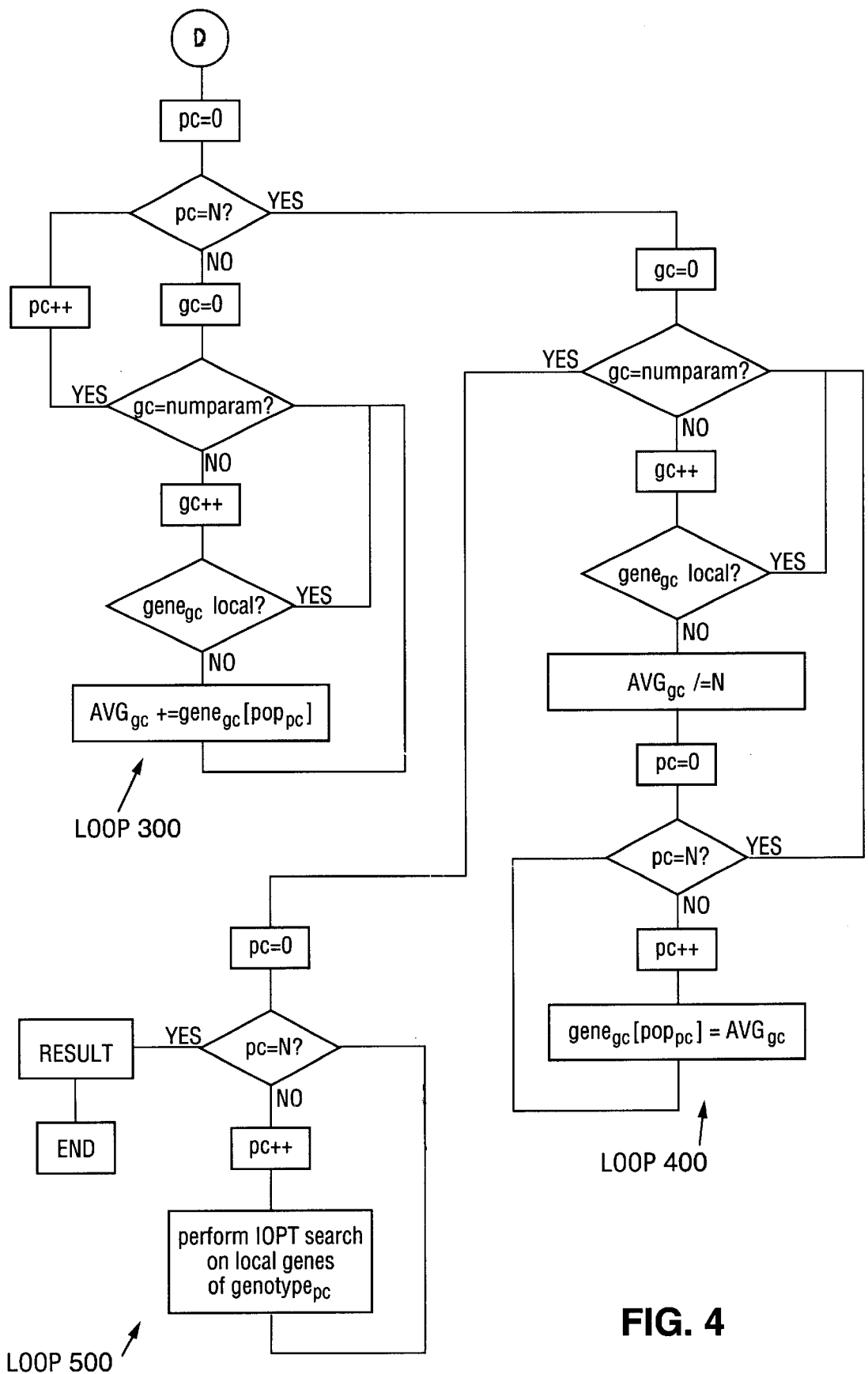
FIG. 4 shows a flow chart illustrating an additional portion of the method shown in FIG. 3 according to present invention.

In step 101, termination criteria are examined, and if the criteria are satisfied, a preferred solution results in the methodology of FIG. 4 being applied ("point D").

The selection of genotypes in step 102 is statistically based upon how closely the theoretical data associated with the genotypes fits with the measured data. The selection is such that it is more likely that a genotype having a high fitness will be selected than one having a low fitness. This type of selection process is sometimes called a weighted lottery. In the preferred embodiment, a newly migrated genotype must reside in the new population for at least one generation before it can be selected again for migration via step 102.

Step 103 moves the selected, migrant genotype to another population domain. The population that receives the migrant genotype may be selected at random or may be restricted to some subset such as the "nearest neighbor" populations. The genotype with the worst fitness in the selected population domain is replaced with the migrant genotype, so long as the replaced genotype is not a recent migrant. If the genotype with the worst fitness is a recent migrant, then the genotype with the worst fitness among those genotypes that are not recent migrants may be used for replacement. In an alternative embodiment, rather than migrating entire selected genotypes, the global genes from selected genotypes in a given domain could be used to replace the global genes in genotypes in a new domain. In this alternative, then, global genes themselves, rather than entire genotypes, would in effect migrate.

In step 104 the fitness of the newly received migrants in each domain is evaluated in the same manner as was done in step 100.

In step 105, counters for each domain, such as counter i, are reset to zero. Counter i counts the number of genotypes which are created in the next generation population. In this part of the routine a new population of genotypes is propagated in each population domain through genetic operations and forms the next generation. In order to count the number of genotypes in the population domain, a counter is initialized for each population domain and thereafter serves to track the number of genotypes which are genetically propagated in the bottom portion of the routine.

In step 106, the counters are compared to the preset values $M_p$. Once all the counters for the populations p are equal to the corresponding $M_p$ values, then the new populations are full and the generation number GEN is incremented by one in step 114. The routine then returns to step 101 to either terminate or begin constructing another generation of genotypes. If the new populations are not full, the routine proceeds to step 108 and evolves one or more new genotypes for the new generation.

In step 108, a genetic operation is selected. The selection among genetic operations will usually be made probabilistically, but could be performed arbitrarily. There are three basic genetic operations, namely direct reproduction, crossover and mutation, as illustrated in FIGS. 5A, 5B, and 5C, although the invention is not strictly limited in this sense. Each of these genetic operations should be employed to some degree to provide a sufficiently random evolution of the genotypes, although this is not strictly required.

For each of the three possible genetic operations, either one or two genotypes are selected from the current population. The genotype selected in step 109 is statistically based upon how closely the theoretical data associated with that genotype "fits" with the measured data. Although the selection is by chance, it is more likely that a genotype having a high fitness F will be selected than one having a low fitness. In the preferred embodiment, the likelihood of being selected is directly proportional to the fitness. By selecting the genotypes in this Darwinian fashion, the population can evolve in a manner so that the genotypes migrate towards progressively better fitting solutions. In addition, by using a weighted, but still random selection process, it is possible to search for best fit solutions over the entire population. This provides a more efficient search of the total solution space than can be achieved using nonlinear least square fitting algorithms that use search strategies that by their nature are much more localized.

The chosen form of genetic operation will be carried out in step 110. The new genotype(s) created by the genetic operation are then written into the new population in step 111, and the counter for the respective population domain is incremented in step 112.

Steps 108 through 112 may be carried out in many different ways without departing from the scope of the invention. For example, the three basic genetic operations are illustrated in FIGS. 5A–5C. If direct reproduction is chosen in step 108a, a single genotype is selected in step 109a. As noted above, this selection is random, but weighted based on fitness. In step 110a, an exact copy of that selected genotype is copied and inserted into a new population (step 111a). The individual counter i for the respective population domain p is then incremented in step 112a and the routine returns to step 106 to propagate more genotypes until the new population is full. Alternatively, the exact copy of the selected genotype may be subjected to genetic mutation before being copied into the new population, as indicated by the dotted line connection B to step 109c.

If crossover is selected in step 108b, then two genotypes are randomly chosen from the current population (step 109b) based on their fitness. Crossover is then carried out in step 110b, meaning that genes from each of the selected genotypes are selected and exchanged, thereby forming two new genotypes which are then written into the new population in step 111b. If crossover is selected, the individual counter i for the respective population domain must be incremented twice in step 112b since two new genotypes are evolved. The routine returns to step 106 to propagate more genotypes until the new population is full. Alternatively, the crossover genotypes may be subjected to genetic mutation before being copied into the new population, as indicated by the dotted line connection B to step 109c.

If mutation is selected, then one genotype is chosen from the current population in step 109c based on its fitness. Some number of genes from the selected genotype are selected and then mutated in step 110c, and the new genotype is written into the new population in step 111c. The individual counter i is then incremented in step 112 and the routine returns to step 106 to propagate more genotypes until the new population is full at which point the generation counter GEN is incremented.

As noted above, the selection of genotypes for use in the genetic operation is generally according to a weighted lottery based on fitness, although it is possible to force a selection through direct intervention. Also, the selection of individual genes to be operated upon is generally random.

As previously discussed, the routine will run until a termination criterion is satisfied in step 101. In practice, the termination criterion is designed to allow the population to evolve for a predetermined number of generations. In this case, such a predetermined number can be selected based on how fast the processor runs and how long the operator is willing to wait for a result. It should be understood that the longer the populations are allowed to evolve, the more likely it is that a good fit will be obtained. Other termination criteria could be established, such as when the fitness of the best genotype of the population does not improve by at least some selected amount δ over the last Q generations. When the termination criteria is satisfied, another routine shown in FIG. 4 is applied ("point D" of FIG. 3).

The routine that begins at point D can be described as follows. In loops 300 and 400, one takes the best genotype from each population domain and finds the average of each global parameter. In other words, for each global parameter one sums the corresponding gene values of the best genotypes from each domain in loop 300 and then divides by the number of domains ("N") to yield a global average in loop 400. For the best genotype in each domain, the gene values corresponding to each global parameter are then reset to this global average also in loop 400. Then in loop 500 one takes the best genotype for each domain and performs a nonlinear least squares optimization for the genes in that genotype that correspond to the local parameters. At the end of this process, for each domain, one has a solution genotype whose global parameter genes are an average of those for the best genotypes of all of the domains and whose local parameter genes are the result of the nonlinear optimization process. As described above, a suitable iterative optimization technique for this purpose is disclosed in "*Multiparameter Measurements of Thin Films Using Beam-Profile Reflectivity,*" Fanton et al., Journal of Applied Physics, Vol. 73, No. 11. p.7035 (1993) and "*Simultaneous Measurement of Six Layers in a Silicon on Insulator Film Stack Using Spectrophotometry and Beam Profile Reflectometry,*" Leng et al., Journal of Applied Physics, Vol. 81, No. 8, p.3570 (1997), which are incorporated by reference.

An alternative to the method shown in loop 500 of FIG. 4 would be to again run a genetic algorithm in each domain during which algorithm the global genes would be held fixed and only the local genes would be allowed to evolve.

Figure 6:
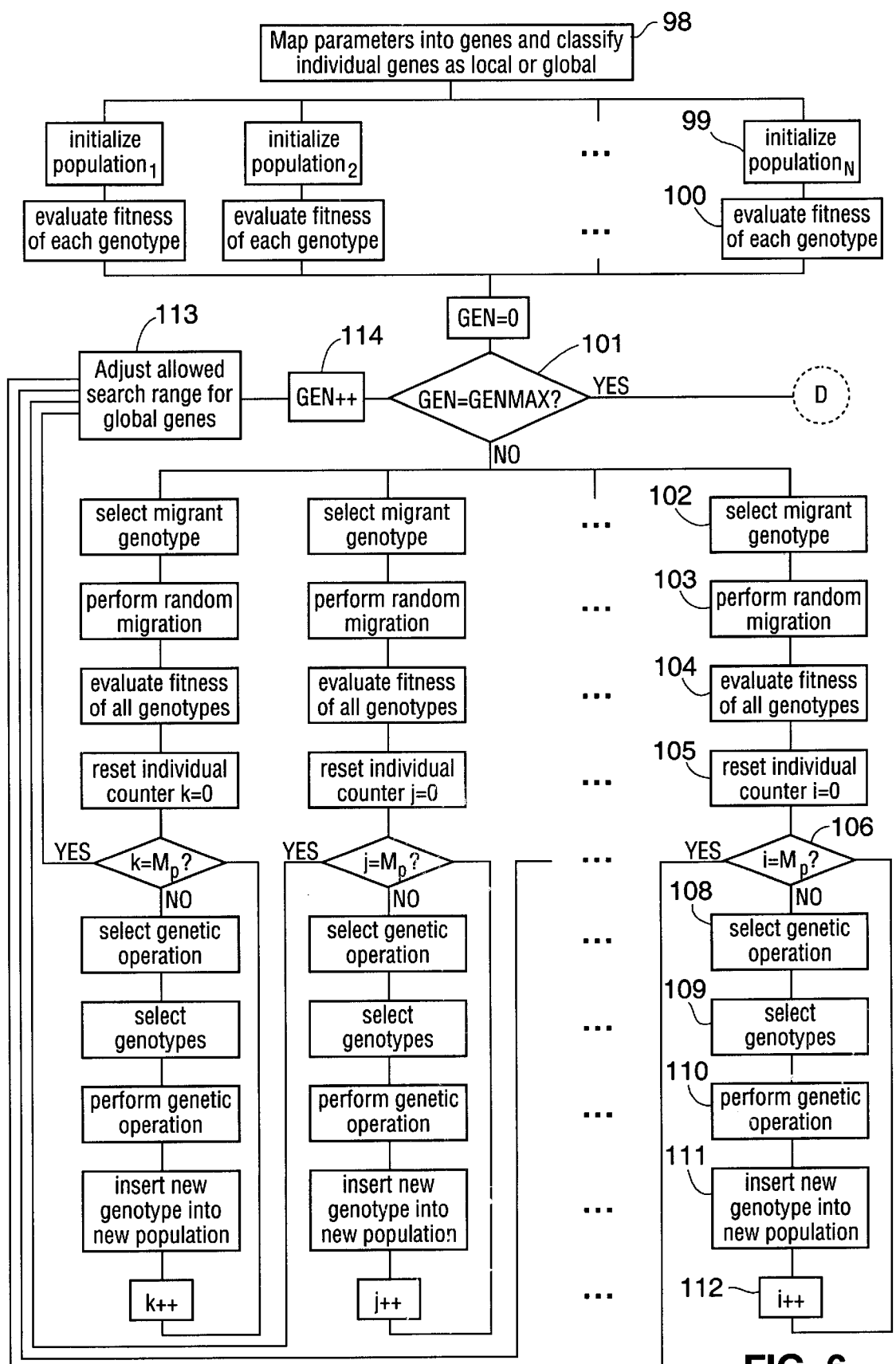
FIG. 6 shows a flow chart illustrating an alternative method according to the present invention.

One expects that, as the domains evolve under the GA, the global genes of the elite genotypes in the different domains will tend to converge in value. For each global parameter, one could test the associated global genes for such a convergence at each generation and then limit the allowed range of values for those global genes based on the degree of convergence obtained thus far. This could be done simply by resetting gene values falling above the allowed range to the range's maximum value, and gene values falling below the allowed range to the range's minimum value. In other words the allowed "search range" for the global genes may be dynamically narrowed as the GA proceeds. This alternative embodiment is shown in FIG. 6 in which the added step 113 prior to the incrementing of the GEN counter represents such a dynamic narrowing of the search range for the global genes as the GA proceeds. After termination of the GA, as indicated by point D', one may optionally proceed to optimize the local genes of the best genotypes in each domain with a nonlinear least squares algorithm as is shown in loop 500 of FIG. 4.

It should be understood that the invention is not intended to be limited by the specifics of the above-described embodiment, but rather defined by the accompanying claims.

We claim:

1. A multidomain method for evaluating parameters of a semiconductor wafer or wafer set comprising:

identifying a group of semiconductor wafer parameters to be evaluated;

mapping the semiconductor wafer parameters into at least one genotype, said genotype comprising a collection of genes, each gene corresponding to a selected one of the group of semiconductor wafer parameters to be evaluated;

defining more than one domain as a collection of genotypes, each domain with its own population of genotypes;

deriving a set of theoretical data for each genotype;

inspecting the semiconductor wafer or wafer set using a beam of radiation and generating therefrom sets of measured data;

comparing a set of measured data to a corresponding set of derived theoretical data for each genotype in each domain in order to determine a level of fitness for each genotype;

migrating genotypes among the domains by selecting at least one genotype from a current domain population and adding it to the population of a different domain;

evolving a next population for each domain by selecting at least one genotype from the current population based on the fitness level of the genotype and performing a genetic operation on the at least one genotype, thereby creating at least one new genotype and adding the at least one new genotype to the next population; and repeating the comparing, migrating, and evolving steps so that for each domain the fittest genotype becomes increasingly more fit.

2. A method as recited in claim 1 wherein the likelihood of selecting a genotype for a genetic operation from a domain population is proportional to the degree to which the derived theoretical data associated with that genotype matches the measured data.

3. A method as recited in claim 1 wherein the likelihood of selecting a genotype for migration from a domain population depends upon the degree to which the derived theoretical data associated with that genotype matches the measured data.

4. A method as recited in claim 1, wherein the level of fitness of a genotype is determined by calculating the fitness as a function of the difference between the theoretical data and the measured data.

5. A method as recited in claim 1, wherein the performing step includes reproducing an identical copy of the at least one genotype.

6. A method as recited in claim 1, wherein the performing step includes selecting a gene from the at least one genotype and mutating the gene.

7. A method as recited in claim 1, wherein the performing step includes selecting corresponding genes in a pair of genotypes and exchanging the genes.

8. A method as recited in claim 6, wherein the step of selecting a gene includes randomly selecting the gene.

9. A method as recited in claim 7, wherein the step of selecting corresponding genes includes randomly selecting the genes.

10. A method as recited in claim 1, wherein the step of inspecting includes measuring one wafer at multiple points with data generated from each point being used to define a set of measured data.

11. A method as recited in claim 1, wherein the step of inspecting includes measuring multiple wafers.

12. A multidomain method for evaluating parameters of a semiconductor wafer or wafer set, comprising:

identifying a group of semiconductor wafer parameters to be evaluated;

mapping the semiconductor wafer parameters into at least one genotype, said genotype comprising a collection of genes, each gene corresponding to a selected one of the group of semiconductor wafer parameters to be evaluated;

defining more than one domain as a collection of genotypes, each domain with its own population of genotypes;

deriving a set of theoretical data for each genotype;

inspecting the semiconductor wafer or wafer set using a beam of radiation and generating therefrom sets of measured data;

comparing a set of measured data to a corresponding set of derived theoretical data for each genotype in each domain in order to determine a level of fitness for each genotype;

migrating genotypes among the domains by selecting at least one genotype from a current domain population and adding it to the population of a different domain;

evolving a new population of genotypes for each domain by selecting at least one genotype from the current domain population based on the fitness of the genotype and performing a genetic operation on the at least one genotype to form at least one new genotype, said genetic operation being selected from one of the following: reproducing an identical copy of the at least one genotype; selecting a gene from the at least one genotype and mutating the gene; or selecting corresponding genes in a pair of genotypes and exchanging the genes, and adding the at least one new genotype to a next population; and repeating the comparing, migrating, and evolving steps so that for each domain the fittest genotype becomes increasingly more fit.

13. A method as recited in claim 12, wherein the step of selecting at least one genotype for evolution includes selecting at least one genotype in proportion to its fitness.

14. A method as recited in claim 12 wherein the likelihood of selecting a genotype for migration from a domain population depends upon the degree to which the derived theoretical data associated with that genotype matches the measured data.

15. A method as recited in claim 12, wherein the step of selecting a gene includes randomly selecting the gene.

16. A method as recited in claim 12, wherein the step of selecting corresponding genes includes randomly selecting the genes.

17. A multidomain method for evaluating parameters of a semiconductor wafer or wafer set comprising:

identifying a group of semiconductor wafer parameters to be evaluated;

mapping the semiconductor wafer parameters into at least one genotype, said genotype comprising a collection of genes, each gene corresponding to a selected one of the group of semiconductor wafer parameters to be evaluated;

dividing the genes into at least two different gene classes, at least one of said gene classes being subject to a migration operation;

defining more than one domain as a collection of genotypes, each domain with its own population of genotypes;

deriving a set of theoretical data for each genotype;

inspecting the semiconductor wafer or wafer set using a beam of radiation and generating therefrom sets of measured data;

comparing a set of measured data to a corresponding set of derived theoretical data for each genotype in each domain in order to determine a level of fitness for each genotype;

applying a migration operation to at least one genotype from a current domain population, said migration operation including a mechanism for moving genes in at least one of said gene classes to the genotype population of a different domain;

evolving a next population for each domain by selecting at least one genotype from the current population based on the fitness level of the genotype and performing a genetic operation on the at least one genotype, thereby creating at least one new genotype and adding the at least one new genotype to the next population; and repeating the comparing, migration operation, and evolving steps so that for each domain the fittest genotype becomes increasingly more fit.

18. A method as recited in claim 17 wherein the likelihood of selecting a genotype for a genetic operation from a domain population is proportional to the degree to which the derived theoretical data associated with that genotype matches the measured data.

19. A method as recited in claim 17 wherein the likelihood of selecting a genotype for migration from a domain population depends upon the degree to which the derived theoretical data associated with that genotype matches the measured data.

20. A method as recited in claim 17, wherein the level of fitness of a genotype is determined by calculating the fitness as a function of the difference between the theoretical data and the measured data.

21. A method as recited in claim 17, wherein the performing step includes reproducing an identical copy of the at least one genotype.

22. A method as recited in claim 17, wherein the performing step includes selecting a gene from the at least one genotype and mutating the gene.

23. A method as recited in claim 17, wherein the performing step includes selecting corresponding genes in a pair of genotypes and exchanging the genes.

24. A method as recited in claim 22, wherein the step of selecting a gene includes randomly selecting the gene.

25. A method as recited in claim 23, wherein the step of selecting corresponding genes includes randomly selecting the genes.

26. A method as recited in claim 17, wherein the permissible range of values for genes in at least one of said gene classes that is subject to a migration operation becomes increasingly narrow as the comparing, migration operation, and evolving steps are repeated.

27. A multidomain method for evaluating parameters of a semiconductor wafer or wafer set, comprising:

identifying a group of semiconductor wafer parameters to be evaluated;

mapping the semiconductor wafer parameters into at least one genotype, said genotype comprising a collection of genes, each gene corresponding to a selected one of the group of semiconductor wafer parameters to be evaluated;

dividing the genes into at least two different gene classes, at least one of said gene classes being subject to a migration operation;

defining more than one domain as a collection of genotypes, each domain with its own population of genotypes;

deriving a set of theoretical data for each genotype;

inspecting the semiconductor wafer or wafer set using a beam of radiation and generating therefrom sets of measured data;

comparing a set of measured data to a corresponding set of derived theoretical data for each genotype in each domain in order to determine a level of fitness for each genotype;

applying a migration operation to at least one genotype from a current domain population, said migration operation including a mechanism for moving genes in at least one of said gene classes to the genotype population of a different domain;

evolving a new population of genotypes for each domain by selecting at least one genotype from the current domain population based on the fitness of the genotype and performing a genetic operation on the at least one genotype to form at least one new genotype, said genetic operation being selected from one of the following: reproducing an identical copy of the at least one genotype; selecting a gene from the at least one genotype and mutating the gene; or selecting corresponding genes in a pair of genotypes and exchanging the genes, and adding the at least one new genotype to a next population; and repeating the comparing, migration operation, and evolving steps so that for each domain the fittest genotype becomes increasingly more fit.

28. A method as recited in claim 27, wherein the step of selecting at least one genotype for evolution includes selecting at least one genotype in proportion to its fitness.

29. A method as recited in claim 27 wherein the likelihood of selecting a genotype for migration from a domain population depends upon the degree to which the derived theoretical data associated with that genotype matches the measured data.

30. A method as recited in claim 27, wherein the step of selecting a gene includes randomly selecting the gene.

31. A method as recited in claim 27, wherein the step of selecting corresponding genes includes randomly selecting the genes.

32. A method as recited in claim 27, wherein the permissible range of values for genes in at least one of said gene classes that is subject to a migration operation becomes increasingly narrow as the comparing, migration operation, and evolving steps are repeated.

33. A method as recited in claim 1 or claim 12 or claim 17 or claim 27 wherein the step of deriving a set of theoretical data for each genotype includes the use of a nonlinear least squares optimization algorithm for selected genotypes.

34. A multidomain process for evaluating parameters of a semiconductor wafer or wafer set comprising:

identifying a group of semiconductor wafer parameters to be evaluated;

inspecting the semiconductor wafer or wafer set using a beam of radiation and generating therefrom sets of measured data, each set of measured data corresponding to a different measurement;

defining more than one search domain, each search domain corresponding to a set of measured data;

applying an iterative search method to each search domain in order to generate a group of optimized parameter values for each search domain, said iterative search method including the steps of:

generating a set of theoretical parameter values associated with each search domain;

deriving a set of theoretical data for each set of theoretical parameter values;

comparing the sets of theoretical data associated with the set of parameter values associated with each search domain to the set of measured data corresponding to each search domain;

generating a new set of theoretical parameter values of each search domain based on the comparing step in a manner so as to identify increasingly more optimal theoretical parameter values for each search domain; and wherein said iterative search method further includes the step of migrating a set of theoretical parameter values from one search domain to another search domain.

35. A method as recited in claim 34, wherein the step of inspecting includes measuring one wafer at multiple points.

36. A method as recited in claim 34, wherein the step of inspecting includes measuring multiple wafers.

37. A method as recited in claim 34 wherein said iterative search method is a genetic algorithm.

\* \* \* \* \*